(12) United States Patent
Allen et al.

(10) Patent No.: US 7,147,604 B1
(45) Date of Patent: Dec. 12, 2006

(54) HIGH Q FACTOR SENSOR

(75) Inventors: Mark Allen, Atlanta, GA (US);
Michael Fonseca, Atlanta, GA (US);
Jason White, Atlanta, GA (US); Jason Kroh, Villa Rica, GA (US); David Stern, Grayson, GA (US)

(73) Assignee: CardioMEMS, Inc., Atlanta, GA (US)

( * ) Notice: Subject to any disclaimer, the term of this patent is extended or adjusted under 35 U.S.C. 154(b) by 439 days.

(21) Appl. No.: 10/215,379

(22) Filed: Aug. 7, 2002

(51) Int. Cl.
*A61B 5/00* (2006.01)

(52) U.S. Cl. ..................................... 600/549

(58) Field of Classification Search ............... 600/549, 600/374, 561, 300, 398, 405, 587; 607/103, 607/122; 244/134 F; 422/1, 28; 340/582, 340/870.16; 29/831; 438/53; 336/83, 200, 336/212, 218, 233; 356/477; 250/227.19; 385/12; 257/419, 254, 417; 324/655, 652, 324/653; 331/66

See application file for complete search history.

(56) References Cited

U.S. PATENT DOCUMENTS

| 2,796,863 | A | 6/1957 | von Wittem |
|---|---|---|---|
| 3,867,950 | A | 2/1975 | Fischell |
| 3,942,382 | A | 3/1976 | Hok |
| 3,958,558 | A | 5/1976 | Dunphy et al. |
| 4,026,276 | A | 5/1977 | Chubbuck |
| 4,127,110 | A | 11/1978 | Bullara |
| 4,206,762 | A | 6/1980 | Cosman |
| 4,207,903 | A | 6/1980 | O'Neill |
| RE30,366 | E | 8/1980 | Rasor et al. |
| 4,237,900 | A | 12/1980 | Schulman et al. |
| 4,354,506 | A | 10/1982 | Sakaguchi et al. |
| 4,378,809 | A | 4/1983 | Cosman |
| 4,485,813 | A | 12/1984 | Anderson et al. |
| 4,494,950 | A | 1/1985 | Fischell |
| 4,521,684 | A | 6/1985 | Gilby et al. |
| 4,596,563 | A | 6/1986 | Pande |
| 4,713,540 | A | 12/1987 | Gibly et al. |
| 4,718,425 | A | 1/1988 | Tanaka et al. |
| 4,796,641 | A | 1/1989 | Mills et al. |
| 4,815,472 | A | 3/1989 | Wise et al. |
| 4,846,191 | A | 7/1989 | Brockway et al. |
| 4,890,623 | A * | 1/1990 | Cook et al. ................. 600/374 |
| 4,899,752 | A | 2/1990 | Cohen |
| 4,913,147 | A | 4/1990 | Fahlstrom et al. |
| 4,934,369 | A | 6/1990 | Maxwell |
| 4,987,897 | A | 1/1991 | Funke |

(Continued)

FOREIGN PATENT DOCUMENTS

CA 1 158 061 6/1983

(Continued)

OTHER PUBLICATIONS

A. Dehennis, K.D. Wise; "A Passive-Telemetry-Based Pressure Sensing System"; NSF Engineering Research Center For Wireless Integrated MicroSystems; Department of Electrical Engineering and Computer Science; The University of Michigan, Ann Arbor, MI 48109-2122 US.

(Continued)

*Primary Examiner*—Max F. Hindenburg
*Assistant Examiner*—Brain Szmal
(74) *Attorney, Agent, or Firm*—Kilpatrick Stockton LLP

(57) ABSTRACT

A sensor for wirelessly determining a physical property within a defined space comprises an electrical resonance and has a high quality factor Q. The quality factor Q is sufficiently high that a signal generated by the sensor can be received outside the defined space. The sensor may optimally have a dielectric coating.

8 Claims, 7 Drawing Sheets

U.S. PATENT DOCUMENTS

| | | | |
|---|---|---|---|
| 5,113,868 A | 5/1992 | Wise et al. | |
| 5,115,128 A | 5/1992 | Cook | |
| 5,129,394 A | 7/1992 | Mehra | |
| 5,165,289 A | 11/1992 | Tilmans | |
| 5,181,423 A | 1/1993 | Philipps et al. | |
| 5,192,314 A | 3/1993 | Daskalakis | |
| 5,207,103 A | 5/1993 | Wise et al. | |
| 5,265,606 A | 11/1993 | Kujawski | |
| 5,353,800 A | 10/1994 | Pohndorf et al. | |
| 5,367,376 A * | 11/1994 | Lagakos et al. | 356/477 |
| 5,373,852 A | 12/1994 | Harrison et al. | |
| 5,411,551 A | 5/1995 | Winston et al. | |
| 5,431,171 A | 7/1995 | Harrison et al. | |
| 5,440,300 A | 8/1995 | Spillman, Jr. | |
| 5,487,760 A | 1/1996 | Villafana | |
| 5,497,099 A | 3/1996 | Walton | |
| 5,515,041 A | 5/1996 | Spillman, Jr. | |
| 5,535,752 A | 7/1996 | Halperin et al. | |
| 5,538,005 A | 7/1996 | Harrison et al. | |
| 5,551,427 A | 9/1996 | Altman | |
| 5,566,676 A | 10/1996 | Rosenfeldt et al. | |
| 5,583,474 A * | 12/1996 | Mizoguchi et al. | 336/83 |
| 5,593,430 A | 1/1997 | Renger | |
| 5,600,245 A | 2/1997 | Yamamoto et al. | |
| 5,626,630 A | 5/1997 | Markowitz et al. | |
| 5,686,841 A | 11/1997 | Stolarczyk et al. | |
| 5,695,155 A * | 12/1997 | Macdonald et al. | 244/134 F |
| 5,702,427 A | 12/1997 | Ecker et al. | |
| 5,703,576 A | 12/1997 | Spillman, Jr. et al. | |
| 5,713,917 A | 2/1998 | Leonhardt et al. | |
| 5,722,414 A | 3/1998 | Archibald et al. | |
| 5,723,791 A | 3/1998 | Koch et al. | |
| 5,743,267 A | 4/1998 | Nikolic et al. | |
| 5,796,827 A | 8/1998 | Coppersmith et al. | |
| 5,807,265 A | 9/1998 | Itoigawa et al. | |
| 5,836,886 A | 11/1998 | Itoigawa et al. | |
| 5,860,938 A | 1/1999 | Lafontaine et al. | |
| 5,899,927 A | 5/1999 | Ecker et al. | |
| 5,935,084 A | 8/1999 | Southworth | |
| 5,942,991 A | 8/1999 | Gaudreau et al. | |
| 5,967,986 A | 10/1999 | Cimochowski et al. | |
| 6,015,386 A | 1/2000 | Kensey et al. | |
| 6,015,387 A | 1/2000 | Schwartz et al. | |
| 6,019,729 A | 2/2000 | Itoigawa et al. | |
| 6,024,704 A | 2/2000 | Meador et al. | |
| 6,025,725 A * | 2/2000 | Gershenfeld et al. | 324/652 |
| 6,030,413 A | 2/2000 | Lazarus | |
| 6,033,366 A | 3/2000 | Brockway et al. | |
| 6,053,873 A | 4/2000 | Govari et al. | |
| 6,076,016 A | 6/2000 | Feierbach | |
| 6,111,520 A * | 8/2000 | Allen et al. | 340/870.16 |
| 6,113,553 A | 9/2000 | Chubbuck | |
| 6,140,740 A | 10/2000 | Porat et al. | |
| 6,159,156 A | 12/2000 | Van Bockel | |
| 6,198,965 B1 | 3/2001 | Penner et al. | |
| 6,201,980 B1 | 3/2001 | Darrow et al. | |
| 6,229,190 B1 * | 5/2001 | Bryzek et al. | 257/419 |
| 6,237,398 B1 | 5/2001 | Porat et al. | |
| 6,239,724 B1 | 5/2001 | Doron et al. | |
| 6,277,078 B1 | 8/2001 | Porat et al. | |
| 6,278,379 B1 | 8/2001 | Allen et al. | |
| 6,287,253 B1 | 9/2001 | Ortega et al. | |
| 6,409,674 B1 | 6/2002 | Brockway et al. | |
| 6,454,720 B1 | 9/2002 | Clerc et al. | |
| 6,645,143 B1 | 11/2003 | Van Tassell et al. | |
| 6,765,493 B1 | 7/2004 | Lonsdale et al. | |
| 6,923,769 B1 | 8/2005 | Nishii et al. | |
| 6,926,670 B1 | 8/2005 | Rich et al. | |
| 6,939,299 B1 * | 9/2005 | Petersen et al. | 600/398 |
| 2002/0188207 A1 | 12/2002 | Richter | |
| 2003/0031587 A1 * | 2/2003 | Hu et al. | 422/28 |
| 2004/0122494 A1 * | 6/2004 | Eggers et al. | 607/103 |
| 2005/0075897 A1 | 4/2005 | Olson et al. | |
| 2005/0085703 A1 | 4/2005 | Behm | |
| 2005/0154321 A1 | 7/2005 | Wolinsky et al. | |

FOREIGN PATENT DOCUMENTS

| | | |
|---|---|---|
| DE | 196 44 858.5 | 10/1996 |
| EP | 0 337 035 | 11/1993 |
| EP | 0 646 365 | 4/1995 |
| WO | WO 83/03348 | 10/1983 |
| WO | WO 90/06723 | 6/1990 |
| WO | WO 95/33517 | 12/1995 |
| WO | WO 97/09926 | 3/1997 |
| WO | WO 97/32518 | 9/1997 |
| WO | WO 97/32519 | 9/1997 |
| WO | WO 97/33513 | 9/1997 |
| WO | WO 99/34731 | 7/1999 |
| WO | WO 00/16686 | 3/2000 |
| WO | WO 01/00089 | 1/2001 |
| WO | WO 01/87137 | 11/2001 |
| WO | WO 01/97908 | 12/2001 |
| WO | WO 03/061504 | 7/2003 |

OTHER PUBLICATIONS

S.R. Vallabhanei, J. Brennan, G. Gilling-Smith, D. Gould, T. How, R. McWilliams, P.L. Harris; Aortic Side Branch Perfusion Alone Does Not Account For High Intra-Sac Pressure After Endovascular Repair (EVAR) In The Absence Of Graft-Related Endoleak; Royal Liverpool University Hospital, Liverpool, UK.

M. Gawenda, J. Heckenkamp, M. Zaehringer, J. Brunkwall; "Intra-Aneurysm Sac Pressure—The Holy Gail of Endoluminal Grafting of AAA"; Eur J Vasc Endovasc Surg. vol. 24, Aug. 2002, pp. 139-145.

G.W.H. Schurink, N.J.M. Arts, J.M Van Baalen, L.J. Schultze Kool, J.H. Van Bockel; "Experimental Study Of The Influence Of Endoleak Size On Pressure In The Aneurysm Sac And The Consequences Of Thrombosis"; British Journal of Surgery 2002, 87, pp. 71-78.

G.W.H. Schurink, N.J.M. Arts, J. Wild, J.M Van Baalen, T.A.M. Chuter, L.J. Schultze Kool, J.H. Van Bockel; "Endoleakage After Silent-Graft Treatment Of Abdominal Aneurysm: Implications On Pressure And Imaging—An In Vitro Study"; Journal of Vascular Surgery, vol. 28, No. 2, pp. 234-241.

B. Sonesson, N. Dias, M. Malina, O. Olofsson, D. Griffin, B. Lindblad, K. Ivancev; "Intra-Aneurysm Pressure Measurements In Successfully Excluded Abdominal Aortic Aneurysm After Endovascular Repair"; Journal of Vascular Surgery, vol. 37, No. 4, Apr. 2003, pp. 733-738.

C.S. Skillern, S.L. Stevens, K.T. Piercy, R.L. Donnell, M. B. Freeman, M.H. Goldman; "Endotension In An Experimental Aneurysm Model"; Journal of Vascular Surgery, vol. 36, No. 4, Oct. 2002, pp. 814-817.

G.D. Treharne, I.M. Loftus, M.M. Thompson, N. Lennard, J. Smith, G. Fishwick, P.R.F. Bell; "Quality Control During Endovascular Aneurysm Repair: Monitoring Aneurysmal Sac Pressure And Superficial Femoral Artery Flow Velocity", J. Endovasc Surg. 1999, 6, pp. 239-245.

M.L. Manwaring, V.D. Malbasa, K.L. Manwaring: "Remote Monitoring Of Intracranial Pressure"; Institute of Concology; Annals Of The Academy Of Studenica Apr. 2001; pp. 77-80.

K. Duriel; "Role of Intrasac Pressure Measurements After EVAR: Can They Be Followed Noninvasively?"; Combined Session: Vascular Surgery and Interventional Radiology; VII 4.1.

R.A. Baum, J.P. Carpenter, C. Cope, M.A. Golden, O.C. Velazquez, D.G. Neschis, M.E. Mitchell, C.F. Barker, R.M. Fairman; "Aneurysm Sac Pressure Measurments After Endovascular Repair Of Abdominal Aortic Aneurysms"; Journal of Vascular Surgery, vol. 33, No. 1, Jan. 2001, pp. 32-41.

P.L. Harris, S. Dimitri; "Predicting Failure Of Endovascular Aneurysm Repair"; Eur J Vas Endovasc Surg, vol. 17, Jan. 1999; pp. 1-2.

G. Akingba, A. Cheng, A. Shum, P. Yang; "An Implantable Pressure Sensor For Aneurysmal Disease".

K.F. Adams, Jr.; "Guiding Heart Failure Care By Invasive Hemodynamic Measurments: Possible Or Useful?"; Journal of Cardiac Failure, vol. 8, No. 2, Apr. 2002, pp. 71-73.

A. Magalski, P. Adamson, F. Galder, M. Boehm, D. Steinhaus, D. Reynolds, K. Vlach, C. Linde, B. Cremers, B. Sparks, T. Bennet; "Continuous Ambulatory Right Heart Pressure Measurments With An Implantable Hemodynamic Monitor: A Multicenter, 12-Month Follow-Up Study Of Patients With Chronic Heart Failure"; Journal of Cardiac Failure, vol. 8, No. 2, Apr. 2002, pp. 63-70.

R. Shabetai; "Monitoring Heart Failure Hemodynamics With An Implantable Device: Its Potential To Improve Outcome"; Journal of the American College of Cardiology; vol. 41, No. 4, Feb. 19, 2003; pp. 572-573.

J.C. Parodi, R. Berguer, L.M. Ferreira, R. Lamura, M.L. Schermerhorn; "Intra-eneurysmal Pressure After Incomplete Endovacular Exclusion"; Journal of Vascular Surgery, vol. 34, No. 5, Nov. 2001, pp. 909-914.

M. Gawenda, J. Heckenkamp, S. Winter, G. Jaschke, J. Brunkwall; "Pressure Is Transmitted Through PTFE And Dacron Grafts Leading To Aneurysm Sac Pressure Endoluminal Grafting of AAA—An In Vitro Study"; Vascular Centre, University of Cologne, Germany.

T. Akin, B. Ziaie, K. Najafi; "RF Telemetry Powering and Control of Hermetically Sealed Integrated Sensors and Actuators"; Center For Integrated Sensors and Circuits; Department of Electrical Engineering and Computer Science; University of Michigan; Ann Arbor, Michigan 48109-2122; pp. 145-148.

H.E. Haynes, A.L. Witchey; "Medical Electronics: The Pill That Talks"; DEP, Camden, N.J.

A. DeHennis, K.D. Wise; "A Double-Sided Single-Chip Wireless Pressure Sensor"; Engineering Research Center For Wireless Integrated MicroSystems; Department of Electrical Engineering and Computer Science; The University of Michigan; Ann Arbor, Michigan 48109-2122.

J. Zhe, R.R. Farmer, V. Modi; "A MEMS Device For Measurement Of Skin Friction With Capacitive Sensing"; Department of Mechanical Engineering, Columbia Univeristy, New York, New York 10027; Microelectronics Research Center, New Jersey Institute of Technology, Newark, NJ 07102.

T. Chuter, K. Ivancev, M. Malina, T. Resch, J. Brunkwall, B. Lindblad, B. Risberg; "Endovascular And Surgical Techniques"; Eur J. Vasc Endovasc Surg vol. 13, Jan. 1997, pp. 85-87.

J.T. Farrar, C. Berkley, V.K. Zworykin; "Telemetering Of Intraenteric Pressure in Man By An Externally Energized Wireless Capsule"; Science, New Series, vol. 131, Issue 3416 (Jun. 17, 1960), 1814.

* cited by examiner

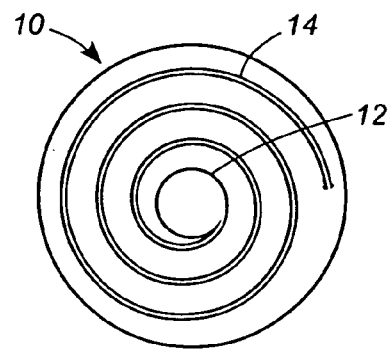
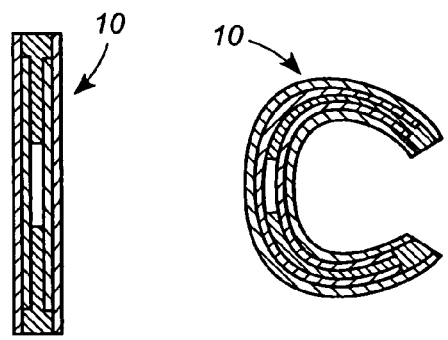
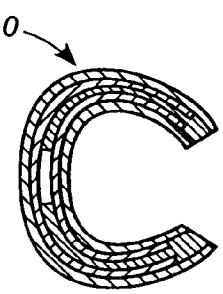
FIG. 1     FIG. 2     FIG. 3
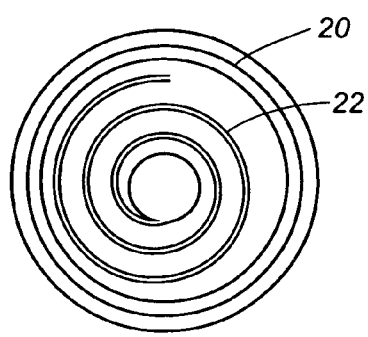
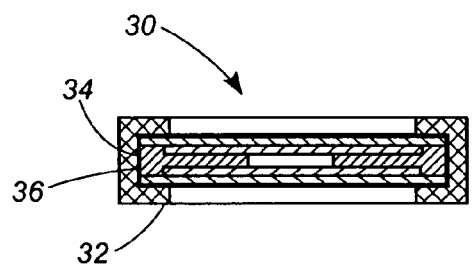
FIG. 4     FIG. 5
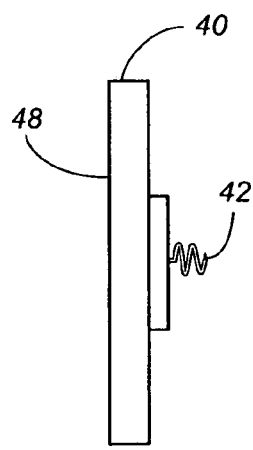
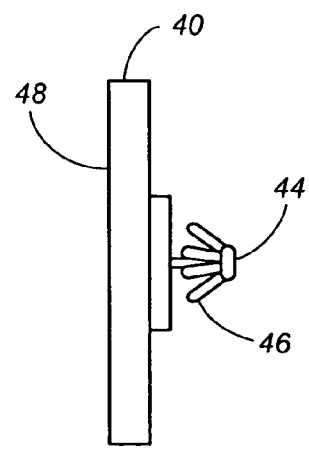
FIG. 6     FIG. 7

HIGH Q FACTOR SENSOR

FIELD OF THE INVENTION

This invention relates to chronically implanted sensors for wirelessly sensing pressure, temperature, and/or other physical properties within the human body. More particularly, the invention concerns a wireless, un-powered micromachined blood pressure sensor that can be delivered using endovascular or simple surgical techniques to the interior of a human artery.

BACKGROUND OF THE INVENTION

Systemic arterial blood pressure measurement provides important diagnostic and health monitoring information, especially for people at risk for hypertension. Blood pressure is also an important measurement in most animal research studies. Intravascular measures of blood pressure, typically via a pressure sensor mounted on a catheter inserted directly into a blood vessel, are considered the "gold standard" for measurement accuracy; however, these intravascular measures require invasive surgery and patient immobilization and cannot be used for simple diagnostic or chronic measurements.

Several methods and techniques have been developed to give physicians, health care workers, and patients themselves the ability to monitor blood pressure. Conventional technology consists of an external pressurized cuff that temporarily occludes an artery in the patient's limb, typically an arm, and means to detect and analyze the Korotkoff sounds or pressure fluctuations as the constriction on the artery is released. Since the auscultatory technique is based on the ability of the human ear or microphone to detect and distinguish sounds, there is a possibility for measurement error due to auditory acuity and sensitivity, outside noise interference, or inconsistent assessment. Other procedures for detecting blood pressure, including oscillometric measurement of vessel pressure against the external cuff, ultrasound, and tonography, are all indirect means of measurement with inaccuracies arising from artifacts, measurement error, patient mobility, or operator consistency, or any combination thereof. Furthermore, proper utilization of the equipment involved in these methodologies requires special training, and each technique is subject to user error.

Implanted sensors provide the most accurate measurement of blood pressure, as the measurement is direct and overcomes the drawbacks of the systems listed above. In the case of severe hypertension, renal insufficiency, or a critical care situation, the benefits of an implanted sensor would warrant the risks of percutaneous techniques. Furthermore, these systems could be implanted in less high risk patient populations when the patients undergo other similar procedures, such as angiography, stent deployment, or balloon angioplasty. Additionally, implantation of these systems in live animal research would provide an accurate and simple means of chronic blood pressure measurement.

Implanted sensors would also allow ambulatory measurements, which provide key insights into diurnal variations in blood pressure, and may provide key information into the underlying disease state and more accurate measurement of a patient's "true" blood pressure (i.e., outside the clinical setting, avoiding the "white coat hypertension" syndrome).

For example, a sensor or transducer placed within a blood vessel or immediately external to the vessel can be used to record variations in blood pressure based on physical changes to a mechanical element within the sensor. This information is then transferred from the sensor to an external device that is capable of translating the data from the sensor into a measurable value that can be displayed. The drawback of this type of sensor is that there must be a physical connection between the sensor and the external device, thus limiting its use to acute settings.

Many types of wireless sensors have been proposed that would allow implantation of the device into the body and then through the appropriate coupling means, so that blood pressure readings can be made over longer periods of interest. One method of manufacturing a sensor capable of measuring pressure is to use a capacitor that is assembled so that the capacitive plates will deform as a result of exposure externally applied stress. This deformation will result in a change in the capacitance that will be proportional to the applied stress. The primary limitation to these type of sensors is that the fabrication methods used to manufacture them do not provide sufficient miniaturization to allow the sensors to be introduced and implanted into an artery using less invasive techniques and the materials used do not provide the appropriate biocompatibility and long term mechanical and electrical durability.

The fabrications methodologies that have been developed in the field of Micro-Electro-Mechanical Systems (MEMS), however, do specifically provide the means for assembling miniaturized sensors capable of measuring a variety of properties including pressure. MEMS devices as described in these patents traditionally use silicon as a substrate for construction of miniature electrical or mechanical structures. The resulting sensors are inherently rigid, severely limiting the ability to manipulate them into temporarily small packages that would provide the means for non-surgical implantation into the human body.

A number of patents detail pressure sensors (some capacitive in nature, some manufactured using MEMS-based technology) that are specifically designed for implantation into the human body. These sensors suffer from many of the limitations already mentioned with the additional concern that they require either the addition of a power source to operate the device or a physical connection to a device capable of translating the sensor output into a meaningful display of a physiologic parameter.

To overcome these two problems (power and physical connection), the concept of an externally modulated LC circuit has been applied to development of implantable pressure sensors. Of a number of patents that describe a sensor design of this nature, Chubbuck, U.S. Pat. No. 6,113,553 is a representative example. The Chubbuck patent demonstrates how a combination of a pressure sensitive capacitor placed in series with an inductor coil provides the basis of a wireless, un-powered pressure sensor that is suitable for implantation into the human body. Construction of an LC circuit in which variations of resonant frequency correlate to changes in measured pressure and which these variations can be detected remotely through the use of electromagnetic coupling are further described in Allen et al., U.S. Pat. No. 6,111,520, incorporated herein by reference.

The device embodied by the Chubbuck patent is manufactured using conventional techniques, thus requiring surgical implantation and thus limiting its applicability to areas that are easily accessible to surgery (e.g., the skull).

Importantly, however, the sensor is not specified as being manufactured using MEMS fabrication technology, and thus no provision is made for appropriate miniaturization of the device that would allow practical and safe introduction and delivery into the body using standard percutaneous approaches.

Thus, there is a need for a method of monitor the systemic arterial blood pressure of living beings in a chronic fashion, such as for the monitoring of severe hypertensive patients or patients at risk for renal failure, or in research studies, where the accuracy of an implanted device is warranted. Furthermore, this method should be accurate, reliable, safe, simple to use, inexpensive to manufacture, convenient to implant and comfortable to the patient.

An ideal method of accomplishing all of the above objectives would be to place a device capable of measuring pressure within or adjacent to an artery. By utilizing an external device to display the pressure being measured by the sensor, a healthcare provider or patient will obtain an immediate readout of blood pressure, which could averaged over time or tracked for diurnal variation.

An example of an implantable pressure sensor designed to monitor blood is shown in Kensey et al, U.S. Pat. No. 6,015,386. While this sensor accomplishes some of the above objectives, it has multiple problems that would make its use impractical. For example, the sensor disclosed in the Kensey patent relies on a mechanical sensing element. Elements of this kind cannot be practically manufactured in dimensions that would allow for endovascular introduction. In addition, this type of pressure sensor would be subject to many problems in use that would limit its accuracy and reliability. One example would be exposure of the mechanical sensing element to body fluids or tissue ingrowth that could disrupt its function. Furthermore, the device fails to account for vascular remolding which would result in baseline drift and could render the device inoperable, as the device requires that the artery be permanently deformed by the clamping action of the sensing element.

Thus, there is a need for a biocompatible, wireless, un-powered pressure sensor that for the purposes of introduction and delivery within the human artery can be manipulated into a smaller shape and size by rolling or folding it into a reduced diameter form and loaded into a small diameter catheter. Then, upon positioning the catheter in the desired location, the sensor can be deployed and secured to the interior of the artery.

OBJECTS OF THE INVENTION

It is an object of this invention to provide an implantable wireless sensor.

It is also an object of this invention to provide a wireless, unpowered micromechanical, flexible sensor that can be delivered endovascularly.

It is additionally an object of this invention to provide an implantable, wireless, unpowered sensor that can be delivered endovascularly to a human artery to measure pressure and/or temperature.

It is a further object of the invention to provide a wireless sensor comprising flexible, biocompatible materials and having a high Q factor.

It is yet a further object of the invention to provide a miniature sensor that can be injected into a patient for heart pressure measurement in a patient's pulmonary artery.

These and other objects of the invention will become more apparent from the discussion below.

SUMMARY OF THE INVENTION

The present invention describes a sensor that can be fabricated using micro-machining techniques and can be implanted into the human body using non-surgical methods for the measurement of physical parameters. Specific target locations could include the interior or exterior of a blood vessel, such as the aorta (preferably just below the renal arteries), or the femoral or the brachial artery. In a preferred embodiment, the device is implanted in the arm (radial or brachial artery), as the relative proximity of these arteries to the surface allows for further reduction in sensor size and ease of taking a blood pressure reading. Furthermore, blood pressure measurements in the brachial artery correlate well with aortic blood pressures.

The sensor according to the invention is fabricated using MicroElectroMechanical Systems (MEMS) technology, which allows the creation of a flexible device that is small, accurate, precise, durable, robust, biocompatible, radio-paque and insensitive to changes in body chemistry, biology or external pressure. This device will not require the use of wires to relay pressure information externally nor need an internal power supply to perform its function.

The MEMS approach to sensor design lends itself to the fabrication of small, flat sensors that can be formed using biocompatible polymers as substrate materials. The pressure sensor described above can then be manipulated into a smaller shape and size by rolling, bending, or folding it into a cylindrical form. This smaller object can then be introduced into the arterial system using endovascular catheter techniques. Once positioned in an artery, the device, either on its own or through the addition or inclusion of metallic elements fabricated from stainless steel or super-elastic or shape memory nitinol alloys, unfurls into a preferred flat shape. The metallic components may also include anchors, hooks, harpoons, coils, barbs or other configurations designed to secure the pressure sensor to the arterial wall and resist displacement due to the interaction of flowing blood. In addition, appropriately biocompatible coatings may be applied to the surface of the sensor to prevent adhesion of biological substances to the sensor that could interfere with it proper function.

The pressure sensor can be manufactured using Micromachining techniques that were developed for the integrated circuit industry. An example of this type of sensor features an inductive-capacitive (LC) resonant circuit with a variable capacitor and is described in Allen et al., U.S. Pat. No. 6,111,520, incorporated herein by reference. In this sensor, the capacitance varies with the pressure of the environment in which the capacitor is placed. Consequently, the resonant frequency of the LC circuit of the pressure sensor varies depending on the pressure of the environment. The pressure sensor is made of completely passive components having no active circuitry or power sources such as batteries. The pressure sensor is completely self-contained, having no leads to connect to an external circuit or power source. Furthermore, these same manufacturing techniques can be used to add additional sensing capabilities, such as the ability to measure temperature by the addition of a resistor to the basic LC circuit.

When introduced into artery, the pressure sensor can provide pressure related data by use of an external measuring device. As disclosed in the Allen et al. patent, several different excitation systems can be used. For example, the sensor can be electromagnetically coupled to a transmitting antenna. Consequently, a current is induced in the sensors, which oscillates at the resonant frequency of the sensor. This oscillation causes a change in the frequency spectrum of the transmitted signal. From this change, the bandwidth and resonant frequency of the particular sensor may be determined, from which the corresponding change in pressure can be calculated.

Accordingly, the present invention provides for an impedance system and method of determining the resonant frequency and bandwidth of a resonant circuit within a particular sensor. The system includes a transmitting antenna, which is coupled to an impedance analyzer. The impedance analyzer applies a constant voltage signal to the transmitting antenna scanning the frequency across a predetermined spectrum. The current passing through the transmitting antenna experiences a peak at the resonant frequency of the sensor. The resonant frequency and bandwidth are thus determined from this peak in the current.

The method of determining the resonant frequency and bandwidth using an impedance approach may include the steps of transmitting an excitation signal using a transmitting antenna and electromagnetically coupling a sensor having a resonant circuit to the transmitting antenna thereby modifying the impedance of the transmitting antenna. Next, the step of measuring the change in impedance of the transmitting antenna is performed, and finally, the resonant frequency and bandwidth of the sensor circuit are determined.

In addition, the present invention provides for a transmit and receive system and method for determining the resonant frequency and bandwidth of a resonant circuit within a particular sensor. According to this method, an excitation signal of white noise or predetermined multiple frequencies is transmitted from a transmitting antenna, the sensor being electromagnetically coupled to the transmitting antenna. A current is induced in the resonant circuit of the sensor as it absorbs energy from the transmitted excitation signal, the current oscillating at the resonant frequency of the resonant circuit. A receiving antenna, also electromagnetically coupled to the transmitting antenna, receives the excitation signal minus the energy which was absorbed by the sensor. Thus, the power of the received signal experiences a dip or notch at the resonant frequency of the sensor. The resonant frequency and bandwidth are determined from this notch in the power.

The transmit and receive method of determining the resonant frequency and bandwidth of a sensor circuit includes the steps of transmitting a multiple frequency signal from a transmitting antenna, and, electromagnetically coupling a resonant circuit on a sensor to the transmitting antenna, thereby inducing a current in the sensor circuit. Next, the step of receiving a modified transmitted signal due to the induction of current in the sensor circuit is performed. Finally, the step of determining the resonant frequency and bandwidth from the received signal is executed.

Yet another system and method for determining the resonant frequency and bandwidth of a resonant circuit within a particular sensor includes a chirp interrogation system. This system provides for a transmitting antenna which is electromagnetically coupled to the resonant circuit of the sensor. An excitation signal of white noise or predetermined multiple frequencies is applied to the transmitting antenna for a predetermined period of time, thereby inducing a current in the resonant circuit of the sensor at the resonant frequency. The system then listens for a return signal which radiates from the sensor. The resonant frequency and bandwidth of the resonant circuit are determined from the return signal.

The chirp interrogation method for determining the resonant frequency and bandwidth of a resonant circuit within a particular sensor includes the steps of transmitting a multi-frequency signal pulse from a transmitting antenna, electromagnetically coupling a resonant circuit on a sensor to the transmitting antenna, thereby inducing a current in the sensor circuit, listening for and receiving a return signal radiated from the sensor circuit, and determining the resonant frequency and bandwidth from the return signal.

In addition, the present invention provides an analog system and method for determining the resonant frequency of a resonant circuit within a particular sensor. The analog system comprises a transmitting antenna coupled as part of a tank circuit which in turn is coupled to an oscillator. A signal is generated which oscillates at a frequency determined by the electrical characteristics of the tank circuit. The frequency of this signal is further modified by the electromagnetic coupling of the resonant circuit of a sensor. This signal is applied to a frequency discriminator which in turn provides a signal from which the resonant frequency of the sensor circuit is determined.

The analog method for determining the resonant frequency and bandwidth of a resonant circuit within a particular sensor includes the steps of generating a transmission signal using a tank circuit which includes a transmitting antenna, modifying the frequency of the transmission signal by electromagnetically coupling the resonant circuit of a sensor to the transmitting antenna, and converting the modified transmission signal into a standard signal for further application.

The above methods lend themselves to the creation of small and simple to manufacture hand-held electronic devices that can be used without complication.

Thus, a simple method of monitoring the pressure within a human artery by inserting a pressure transducer using a catheter and using a small, hand-held read device to measure the pressure easily, safely, inexpensively and accurately is disclosed. Also included is a method of introducing the sensor into the body by using the steps of folding or rolling the sensor into a cylinder, loading it into a catheter and deploying into the artery by allowing it to unroll or unfold, either by itself or preferably facilitated by the incorporation of a super-elastic alloy component. The same super-elastic element also provides the means to permanently securing the device to the interior of the artery.

Delivery of the device of the invention to an artery may be accomplished as follows: Using the standard Seldinger technique, the physician gains access to the patient's artery and places a vessel introducer with a hemostatic valve. A coaxial delivery catheter consisting of two hollow extruded polymeric catheters, the smaller of the two disposed inside the larger one, is inserted through the introducer and advanced distally until its tip is located in the segment of the artery within which it is desirable to place the sensor. The smaller catheter has an annular space to hold a folded sensor, which is released when the outer catheter is withdrawn proximally.

In an alternative delivery procedure the sensor can be loaded into the annular space between two, inner and outer catheters by inserting the sensor into a longitudinal slit cut into the outer catheter and attaching a tab on the sensor's surface into a slot cut into the inner coaxial catheter. By rotation of the inner tube, the sensor will be retracted through the slit and positioned in the annular space between the two tubes. To deploy the device, the rotation of the inner tube is reversed and the sensor emerges through the slit of the outer catheter. There are two specific advantages to this deployment mechanism. First, the sensor can be packaged and stored in a flat configuration. This is desirable since long term storage in a pre-loaded curved geometry could make it more difficult for the sensor to re-establish the flat arrangement that is optimal for effective electro-magnetic inductive coupling with the external read-out unit. The second advantage is that by cutting the longitudinal slit at angle that is offset from the main axis of the outer tube, the sensor will be biased into a planar configuration as it is forced through the slit during the deployment process.

In an another version of the delivery mechanism, the sensor (ring shaped or flat) could be crimped or otherwise mounted on an intravascular balloon catheter, common in the art, and delivered to the target location. This balloon catheter is then inflated, forcing the sensor in contact with the vessel wall where it attaches as previously described.

A further alternate delivery mode would be to load a folded sensor within a self-expanding stent constructed from a thermal memory metal such as nitinol. These types of devices are well known in the art. The nitinol stent would be introduced into the artery and allowed to expand using the standard techniques. As the stent expands, the sensor would unfold into its desirable flat shape. The stent, which is held fixed against the arterial wall due to the self-expanding nature of the nitinol materials exerting a constant circumferential force, serves as the mechanism to keep the sensor fixed in a specific position within the vasculature.

In another delivery method, a sensor according to the invention could be attached to and implanted or inserted in combination with a vascular closure device, such as are commonly used after a procedure such as angioplasty. The sensor could be positioned within or attached to a sealing plug or member that is positioned within the artery that is sealed.

For extravascular sensor deployment, simple surgical techniques known to the art expose the target artery. The sensor is placed in intimate contact with the external surface of the vessel, either through clamping around the vessel or via the previously noted anchors, hooks, harpoons, coils, barbs or other shapes and configurations of metallic elements to secure the pressure sensor to the artery wall.

In a further embodiment a smaller version of the sensor can be injected into a site within the patient's vasculature wherein the sensor would lodge in a minor artery or capillary. For example, a small sensor could be injected to a site in or near a patient's lung where the sensor would be positioned in the capillaries that lead to the patient's pulmonary artery, to measure pressure. The resulting information would calculate closely to the actual pressure of the patient's pulmonary artery.

BRIEF DESCRIPTION OF THE DRAWINGS

FIG. 1 is a front view of an embodiment of the invention;

FIG. 2 is a lateral view of the embodiment of the invention shown in FIG. 1;

FIG. 3 is a lateral view of an embodiment of the invention of FIG. 1 folded for delivery;

FIG. 4 is a front view of another embodiment of the invention;

FIG. 5 is a lateral view of a yet further embodiment of the invention;

FIGS. 6 and 7 are each a lateral view of an embodiment of the invention with an anchoring mechanism;

DETAILED DESCRIPTION OF THE INVENTION

Figure 8:
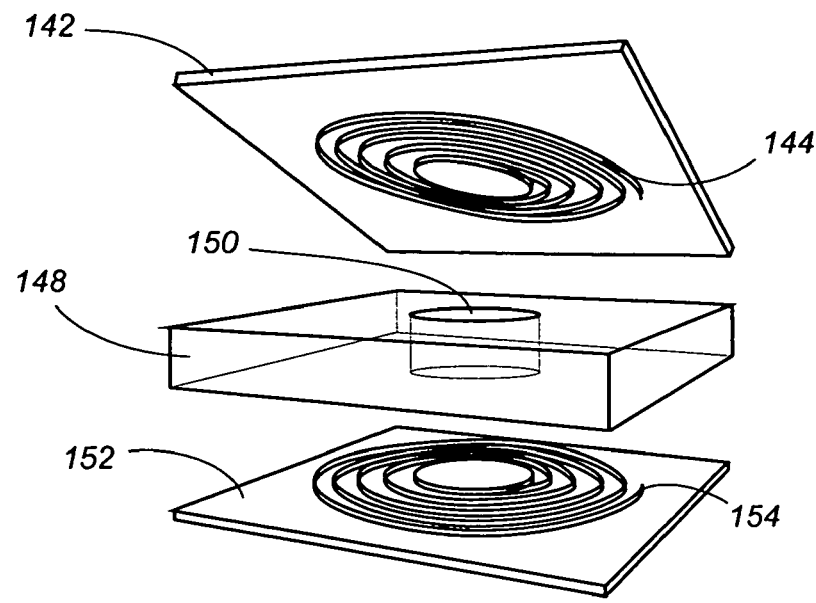
FIG. 8 is an exploded schematic representation of construction of one embodiment of a sensor.

The invention can perhaps be better understood by referring to the drawings. One embodiment of a sensor according to the invention is shown in FIGS. 1, 2, and 3, where a disc-shaped sensor 10 comprises a capacitor disk 12 and a wire spiral 14. FIG. 2 is a lateral view of sensor 10, and FIG. 3 is a lateral view of sensor 10 in a folded configuration for insertion. The fact that sensor 10 is sufficiently flexible to be folded as shown in FIG. 4 is an important aspect of the invention.

In FIG. 4 a ring 20 comprised of a shape memory alloy such as nitinol has been attached to, for example, with adhesive, or incorporated into, for example, layered within, a sensor 22.

FIG. 5 is a lateral cross-sectional view of a circular sensor 30 having a ring 32 comprised of a shape memory alloy such as nitinol encompassing the outer edge 34 of sensor 30. Ring 32 preferably is attached to outer edge 34 by a suitable physiologically acceptable adhesive 36, such as an appropriate epoxy or cyanoacrylate material. Preferably the ring will be radiopaque.

The size of the circular sensors of the invention will vary according to factors such as the intended application, the delivery system, etc. The circular sensors are intended to be from about 0.5 to about 3 cm in diameter, with a thickness of from about 0.05 to about 0.30 in. When a ring 32 is employed, the thickness of the ring, i.e., the width of the outside surface 38, will preferably be from about 1.5 to about 3.5 times the thickness of the sensor.

FIGS. 6 and 7 each represent a lateral view of a sensor with an anchoring member. In FIG. 6 sensor 40 has a screw/coil 42, and in FIG. 7 sensor 40 has an anchor 44 with umbrella-like projections 46. When pressure is applied to the flat side 48 of sensor 40, anchor 42 or 44 will penetrate a vessel wall, organ wall, or other substrate to cause sensor 36 to remain in a desired position or location. Alternatively, an anchoring mechanism such as is shown in FIGS. 6 and 7 could be attached to ring 32 in FIG. 5.

The pressure sensor of the invention can be manufactured using Micro-machining techniques that were developed for the integrated circuit industry. An example of this type of sensor features an inductive-capacitive (LC) resonant circuit with a variable capacitor, as is described in Allen et al., U.S. Pat. No. 6,111,520, all of which is incorporated herein by reference. The sensor contains two types of passive electrical components, namely, an inductor and a capacitor. The sensor is constructed so that the fluid pressure at the sensor's surface changes the distance between the capacitor's parallel plates and causes a variation of the sensor's capacitance.

In an embodiment the sensor of the invention is constructed by laminating several layers of material together, as shown, for example, in FIG. 8. A first layer 142 is fabricated from a sheet of polyimide film (e.g., KAPTON, available from Du Pont) upon which a micro-machined copper pattern 144 is deposited. Pattern 144 preferably consists of a circular conductive segment in the center of the sheet surrounded by a spiral coil. A second layer 148 comprises a sheet of flexible adhesive through which hole 150 has been cut in the center. (Optionally there may be more than one such layer 148.) A final layer 152 is another sheet of polyimide film with a copper pattern 154 that is a mirror image of pattern 144. When assembled, the first, second, and third layers are aligned such that the holes in the middle adhesive layers are centered between the circular conductive segments in the middle of the two outer polyimide layers 142 and 152. In this way a capacitor (defined as an electric circuit element used to store charge temporarily, consisting in general of two metallic plates separated and insulated from each other by a dielectric) is formed. At the same time, the two metal spirals on the polyimide sheets 142 and 152 form an inductor component of a miniature electrical circuit.

The sensor exhibits the electrical characteristics associated with a standard LC circuit. An LC circuit is simply a closed loop with only two elements, a capacitor and an inductor. If a current is induced in the LC loop, the energy in the circuit is shared back and forth between the inductor and capacitor. The result is an energy oscillation that will vary at a specific frequency. This is termed the resonant frequency of the circuit and it can be easily calculated as its value is dependent on the circuit's inductance and capacitance. Therefore, a change in capacitance will cause the frequency to shift higher or lower in linear proportion to the change in the value of capacitance.

As noted above, the capacitor in the assembled pressure sensor consists of the two circular conductive segments separated by an air gap. If a pressure force is exerted on these segments it will act to deform the outer polyimide sheet and move the two conductive segments closer together. This will have the effect of reducing the air gap between them which will consequently change the capacitance of the circuit. The result will be a shift in the circuit's resonant frequency that will be in direct proportion to the force applied to the sensor's surface.

Because of the presence of the inductor, it is possible to electromagnetically couple to the sensor and induce a current in the circuit. This allows for wireless communication with the sensor and the ability to operate it without the need for an internal source of energy such as a battery. Thus, if the sensor is located within the interior of an artery, it will be possible to determine the pressure of blood within the artery in a simple, non-invasive procedure by remotely interrogating the sensor, recording the resonant frequency and converting this value to a pressure measurement. The readout device generates electromagnetic energy that penetrates through the body's tissues to the sensor's implanted location. The sensor's electrical components absorb a fraction of the electromagnetic energy that is generated by the readout device via inductive coupling. This coupling induces a current in the sensor's circuit oscillates at the same frequency as the applied electromagnetic energy. Due to the nature of the sensor's electromechanical system there exists a frequency of alternating current at which the absorption of energy from the readout device is at a minimum. This frequency is a function of the capacitance of the device. Therefore, if the sensor's capacitance changes, so will the frequency at which it minimally absorbs energy from the readout device. Since the sensor's capacitance is mechanically linked to the fluid pressure at the sensor's surface, a measurement of this frequency by the readout device gives a relative measurement of the fluid pressure. If calibration of the device is performed, then an absolute measurement of pressure can be made. See, for example, the extensive discussion in the Allen et al. patent, again incorporated herein by reference, as well as Gershenfeld et al., U.S. Pat. No. 6,025,725, incorporated herein by reference.

The pressure sensor is made of completely passive components having no active circuitry or power sources such as batteries. The pressure sensor is completely self-contained having no leads to connect to an external circuit or power source. Furthermore, these same manufacturing techniques can be used to add additional sensing capabilities, such as the ability to measure temperature by the addition of a resistor to the basic LC circuit.

Figure 9:
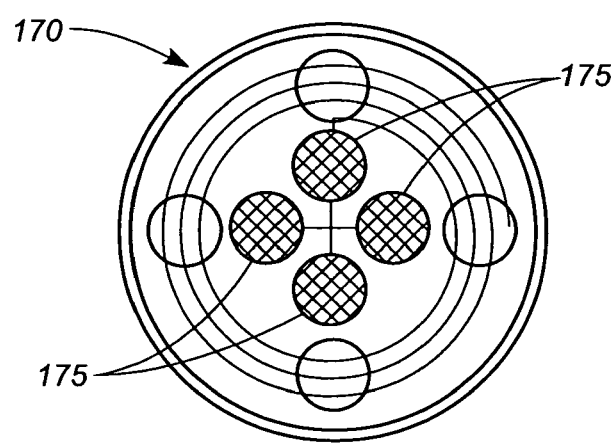
FIG. 9 is a schematic representation of an embodiment of the invention with distributed capacitance.

Several alternative configurations of the LC circuit design can be considered to address specific biological and manufacturing issues. For example, in one embodiment of the sensor the capacitor element consists of two plates that are separated by a suitable dielectric material, such as air, inert gas, fluid or a vacuum. To ensure the long term integrity of the sensor, various coatings could be applied to the surface or between the polymeric layers used to form the sensor. These coating can be used to provide a hermetic seal that will prevent leakage of body fluids into the cavity or permeation of the cavity material (gas, vacuum or fluid) out of the sensor. In another embodiment of the invention, shown in FIG. 9, a sensor 170 has a multitude of capacitors 175 formed either as separate elements or as an array. In such a distributed capacitance configuration, there can be a more accurate and more sensitive measurement of pressure.

It is within the scope of the invention that the frequency response to the sensor will be in the range of from about 1 to about 200 MH$_z$, preferably from about 1 to about 100 MH$_z$, and more preferably from about 2 to about 90 MH$_z$, with a Q factor from about 5 to about 80, preferably from about 10 to about 70, more preferably from about 10 to 60.

In a further embodiment of the invention there is no direct electrical connection between the two sides of the LC circuit. Referring again to the sensor described in the Allen et al. patent, the device is constructed using multiple layers upon lie the necessary circuit elements. Disposed on the top and bottom layer are metal patterns constructed using micro-machining techniques which define a top and bottom conductor and a spiral inductor coil. To provide for an electrical contact between the top and bottom layers small vias or holes are cut through the middle layers. When the layers are assembled, a metal paste is forced into the small vias to create direct electrical connections or conduits. However, experimentation has shown that due to parasitic capacitance that is created between the top and bottom inductor coils, a vialess operational LC circuit can be created. This absence of via holes represents a significant improvement to the sensor in that it simplifies the manufacturing process and, more importantly, significantly increases the durability of the sensor making it more appropriate for use inside the human body.

Figure 10:
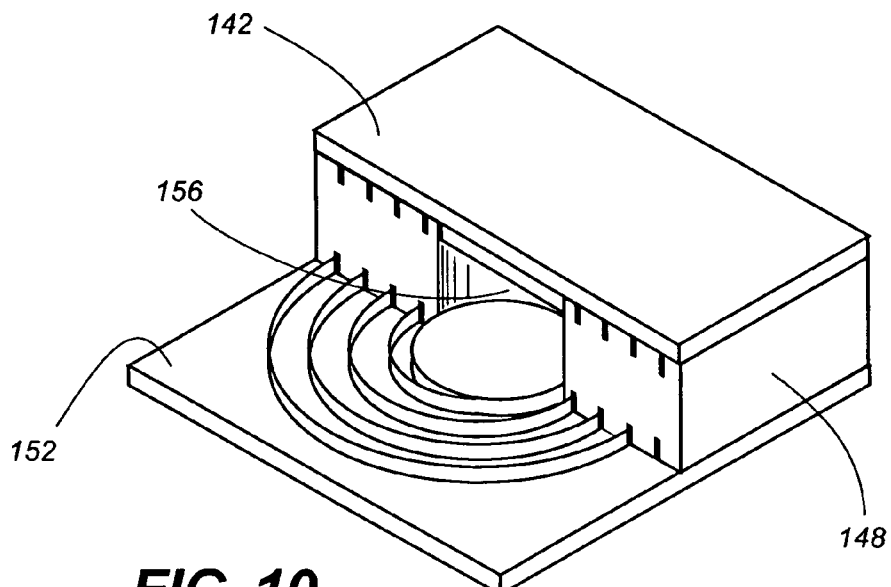
FIGS. 10 and 11 are each a schematic, partial cross-sectional view of an embodiment of a sensor according to the invention.
Figure 11:
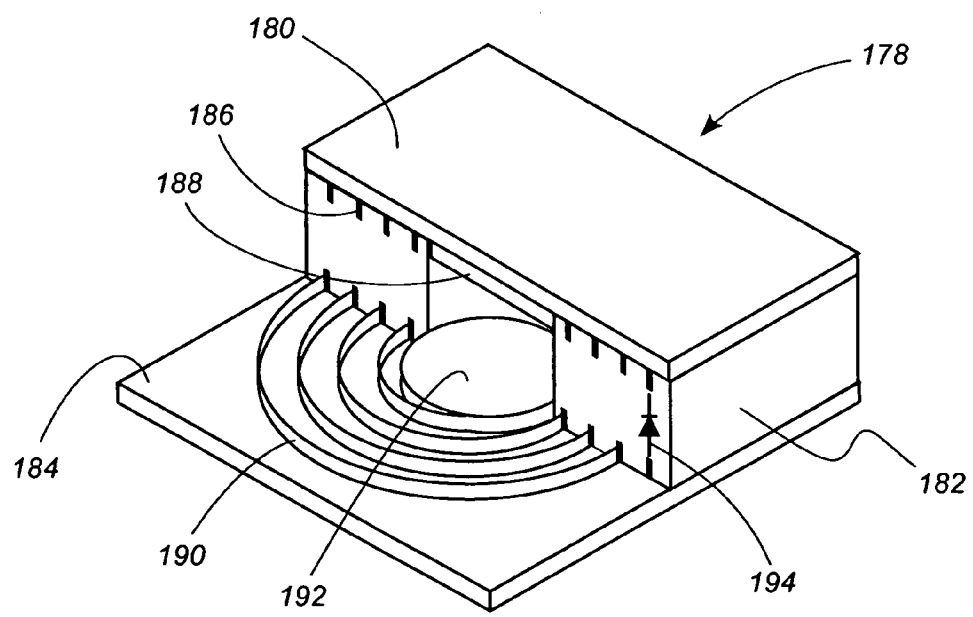

FIG. 10 is a partial cross-sectional review of the sensor shown in FIG. 8, where first layer 142, second layer 148, and third layer 152 are sandwiched together. A cylindrical space 156 comprises a pressure sensitive capacitor. No via holes are present. The sensor 178 shown in FIG. 11 comprises a first polyimide layer 180, a second, adhesive layer 182, and a third, polyimide layer 184. First layer 180 has a copper pattern comprising a coil 186 and a disk 188, and third layer 184 comprises a coil 190 and a disk 192. A cylindrical space 196 comprises a pressure sensitive capacitor. A diode 194 connected between coils 186 and 190 creates a non-linear sensor, i.e., a sensor where the frequency change is non-linear as compared to a change in pressure.

The design of the sensor is not limited to a specific geometric configuration. In the specific example noted above the inductor component is described as a spiral coil. Other embodiments of the sensor could utilize oval, rectangular or an amorphous shape. Specific electrical, mechanical and biologic advantages could be obtained by employing these various geometric designs. By way of example, a rectangular shaped sensor in which the ratio of length to width was greater than four would greater lend itself to catheter based delivery as is would minimize the radius of curvature required to position the folded device within a small diameter catheter. Alternatively, a more elaborate shape, such as one resembling the petals of a flower, would lend itself to more complex folding patterns that could facilitate delivery to specific anatomical location within an artery. For example, in FIGS. 12 and 13, a flower-shaped sensor 208 has a capacitor surface 210 connected to a wire 212 that partly follows the outer configuration of sensor 208. Petals 214 fold so that sensor 208 with a distal anchor 216 can be "loaded" into a catheter 218. When the distal end 220 of catheter 218 is in position, a pushing rod member 222 is pushed distally to cause sensor 208 to be released from catheter 218 and attach to the inner surface of an artery (not shown).

In a preferred embodiment of the invention a foldable sensor is delivered to a patient's artery in the distal end of a delivery catheter. The sensor can be regularly- or irregularly-shaped so that outer portions of the sensor can fold to about a 90° angle as compared to a relatively flat, middle portion of the sensor.

Figure 12:
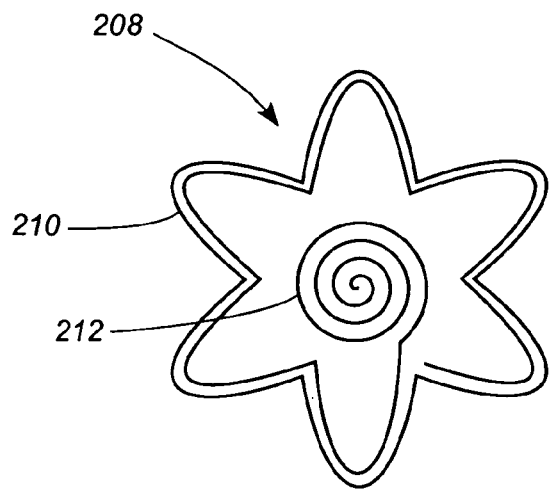
FIG. 12 is a schematic representation of an alternate shape for an embodiment of the invention.

Another embodiment of a sensor is shown in FIG. 12, where circular sensor 230 comprises flexible cut-outs 232. The first outer layer 234 comprises a polymide substrate with a copper pattern comprising a coil 240 and several, from 2 to 6, disks 242 to form pressure sensitive capacitors. Sensor 230 also comprises at least one adhesive layer (not shown) and a third outer layer corresponding to the first outer layer (not shown). Preferably sensor 230 has at least one diode connecting the copper coils of the first and third layers.

Figure 13:
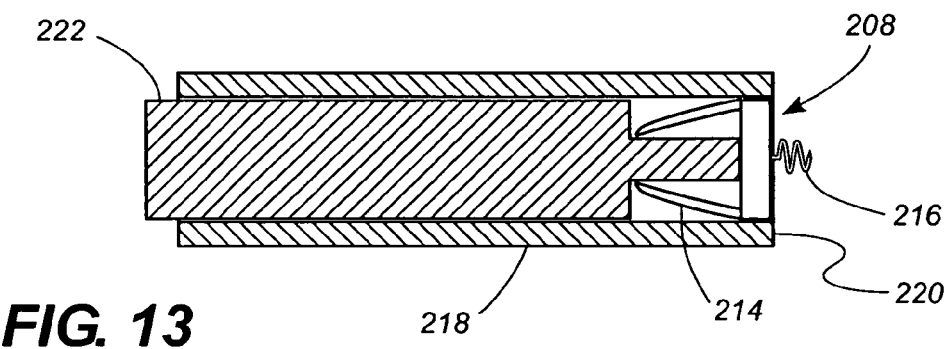
FIG. 13 is a cross-sectional view of the distal end of a delivery catheter with the embodiment shown in FIG. 12.
Figure 14:
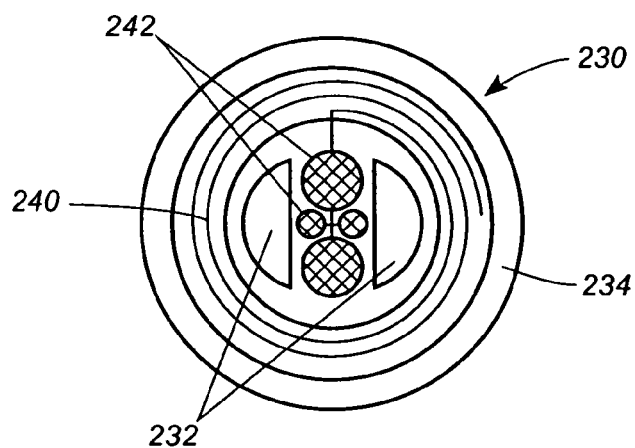
FIG. 14 is a schematic of another sensor according to the invention.
Figure 15:
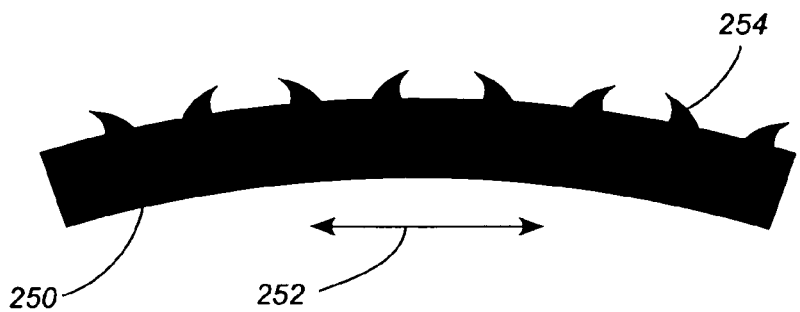
FIG. 15 is a schematic representation of another, preferred embodiment of the invention.

The flexible cut-outs 232 facilitate, among other things, folding of sections of sensor 230 for placement in, or arrangement upon, a delivery catheter, such as in FIG. 13. The sections can also be folded to create either a "Z" shape or, for example, a "U" shape, for other applications. It is within the scope of the invention that variously numbered and shaped cut-outs could be used for particular applications.

While a preferred delivery system is described above, it is within the scope of the invention that other delivery systems could be employed. Other such delivery systems are described in, for example, co-pending, commonly assigned U.S. patent application Ser. No. 10/054,671, filed Jan. 22, 2002, incorporated herein by reference.

A preferred embodiment of the invention and a preferred delivery system are described in FIGS. 15 to 20. A pressure sensor 250 has a slightly curved cross-section in a lateral direction 252. In an especially preferred embodiment sensor 250 has projections 254, which are preferably comprised of a rigid or semi-rigid metallic or polymeric material.

Figure 16:
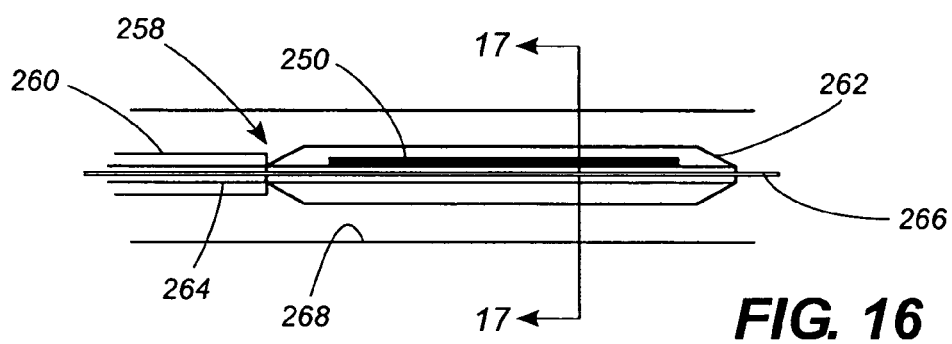
FIG. 16 is a partly cross-sectional view of a preferred delivery system according to the invention.
Figure 17:
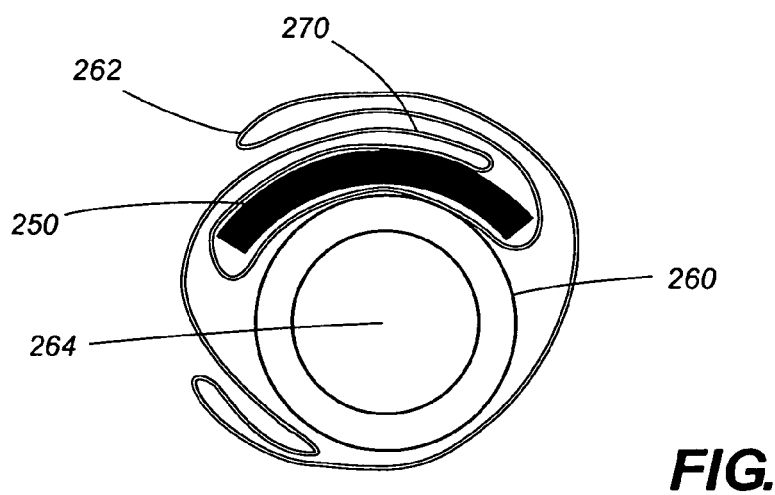
FIG. 17 is a cross-sectional view of FIG. 16 along the line 17—17.

Sensor 250 is loaded onto a balloon dilatation catheter 258, which comprises a catheter shaft 260 and a dilatation balloon 262. Balloon dilatation catheter 258 has a lumen 264, so that balloon dilatation catheter 258 can be advanced over guidewire 266 to a position within an artery 268, as shown in FIG. 16. A cross-sectional view across line 17—17 in FIG. 17 shows sensor 250 positioned within folds 270 of dilatation balloon 262.

Figure 18:
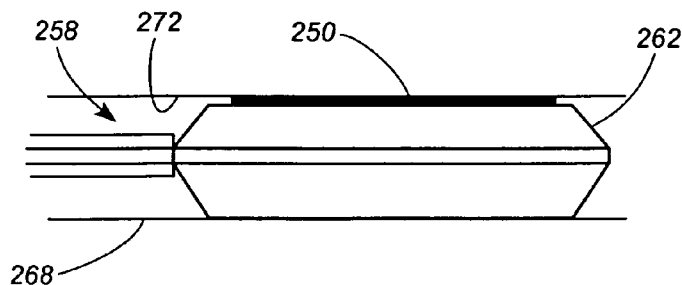
FIG. 18 is a partly cross-sectional view of the delivery system of FIG. 16 with an inflated balloon.
Figure 19:
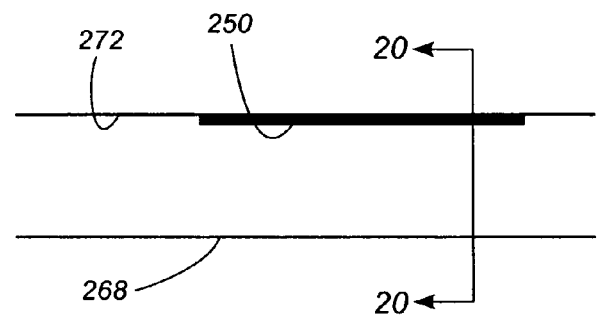
FIG. 19 is a longitudinal cross-sectional view of a delivered sensor.
Figure 20:
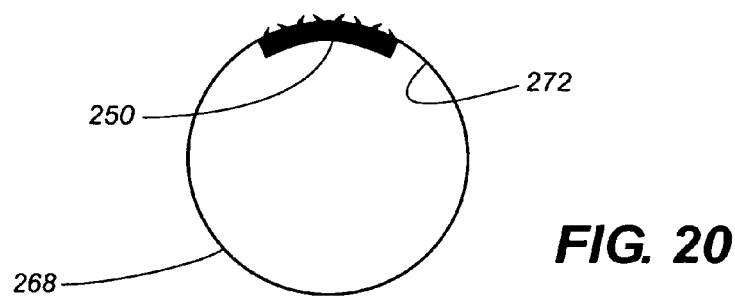
FIG. 20 is a cross-sectional view of FIG. 19 along the line 20—20.

In FIG. 18 dilatation balloon 262 of dilatation balloon catheter 258 has been inflated to press the outer surface of sensor 250 against the inner wall 272 of artery 268. After dilatation balloon 262 is deflated and balloon dilatation catheter 258 is withdrawn, as in FIG. 19, sensor 250 remains, attached to inner wall 272. A lateral cross-sectional view across line 20—20 is shown in FIG. 20.

A significant design factor that relates to the performance of the sensor and the operation of the system is the Quality factor (Q) associated with the sensor. The value of Q is one of the key determinates as to how far from the sensor the external read-out electronics can be located while still maintaining effective communication. Q is defined as a measure of the energy stored by the circuit divided by the energy dissipated by the circuit. Thus, the lower the loss of energy, the higher the Q.

In operation, energy transmitted from the external read-out electronics will be stored in the LC circuit of the sensor. This stored energy will induce a current in the LC loop which will cause the energy to be shared back and forth between the inductor and capacitor. The result is an oscillation that will vary at the resonant frequency of the LC circuit. A portion of this ocscillating energy is then transmitted out of the sensor back to the receiving antenna of the read-out electronics. In high Q sensors, most of the stored energy is available for transmission back to the electronics, which allows the distance between the sensor and the receiving antenna to be increased. Since the transmitted energy will decay exponentially as it travels away from the sensor, the lower the energy available to be transmitted, the faster it will decay below a signal strength that can be detected by the receiving antenna and the closer the sensor needs to be situated relative to the receiving electronics. In general then, the lower the Q, the greater the energy loss and the shorter the distance between sensor and receiving antenna.

The Q of the sensor will be dependent on multiple factors such as the shape, size, diameter, number of turns, spacing between turns and cross-sectional area of the inductor component. In addition, Q will be greatly affected by the materials used to construct the sensors. Specifically, materials with low loss tangents will provide the sensor with higher Q factors.

The implantable sensor accending to the invention is preferably constructed of various polymers that provide the required flexibility, biocompatibility and processing capabilities. Preferably the materials used are flexible, biocompatible, and result in a high Q factor. The example described above indicates that KAPTON, a polyimide, was used. However, suitable materials include polyimides, polyesters (e.g., polyethylene terephthalate), liquid crystal polymers (LCP), and polytetrafluoroethylene (PTFE) and co-polymers thereof. Examples of useful liquid crystal polymers include, but are not limited to, wholly aromatic polyesters such as polybenzoate-naphthalate; polybenzoate-terephthalate; bisphenol-isophthalate; polybenzoate-terephthalate-ethylene glycol; and polynaphthalate-amino terephthate. These materials are considered dielectrics, that is, they are poor conductors of electricity (have a low dielectric constant), but are efficient supporters of electrostatic fields. An important property of dielectric materials is their ability to support an electrostatic field while dissipating minimal energy. The lower the dielectric loss (the proportion of energy lost), the more effective the dielectric material. For a lossy dielectric material, the loss is described by the property termed "loss tangent." A large loss tangent reflects a high degree of dielectric absorption.

As indicated in FIGS. 8 and 10, the middle layer can comprise an adhesive. Useful adhesives include flexible, biocompatible materials such as an epoxy or acrylic adhesive.

Of the materials listed above, LCPs and PTFE have the lowest loss tangents, and construction of pressures sensors from these materials produces the highest Q factor. As an example, an LC circuit pressure sensor similar to the embodiment shown in FIG. 8 was assembled using successive layers of the following materials: polyimide/copper, acrylic adhesive, polyimide, acrylic adhesive, and copper/polyamide. When electrically characterized, the Q of this sensor was approximately 30. A second sensor of the exact same geometry was then fabricated using the following alternate construction: LCP/copper, PTFE/epoxy adhesive (speedboard), and copper/LCP. When tested, this sensor demonstrated a Q factor of 48. Since Q is a logarithmic function, this represents a significant boost that translates into a substantial increase in sensor to read-out electronics distance. Alternatively, LCPs can adhere to themselves, thus eliminating the need for a PTFE/epoxy adhesive layer. In a preferred embodiment of the invention, the sensor construction could be LCP/copper, LCP, copper/LCP. This sensor would be easier to construct and would also have even an higher Q factor.

With regard to operation within the human body, there is a second important issue related to Q, namely, that blood and body fluids are conductive mediums and are thus particularly lossy. The consequence of this fact is that when a sensor is immersed in a conductive fluid, energy from the sensor will dissipate, substantially lowering the Q and reducing the sensor-to-electronics distance. For example, the sensors described above were immersed in saline (0.9% salt solution), and the measured Q decreased to approximately 10. It has been found that such loss can be minimized by insulating the sensor from the conductive liquid. This can be accomplished, for example, by encapsulating the sensor in a suitable dielectric material. However, potential encapsulation material must have the flexibility and biocompatibility characteristics of the sensor material and also be sufficiently compliant to allow transmission of fluid pressure to the pressure sensitive diaphragm. A preferred material for this application is polydimethylsiloxane (silicone).

As an example, a thin (i.e., 200 micron) coating of silicone was applied to the LCP sensor detailed above. This coating provided sufficient insulation to maintain the Q at 40 in a conductive medium. Equally important, despite the presence of the silicone, adequate sensitivity to pressure changes was maintained and the sensor retained sufficient flexibility to be folded for endovascular delivery. One additional benefit of the silicone encapsulation material is that it can be loaded with a low percentage (i.e., 10–20%) of radio-opaque material (e.g., barium sulfate) to provide visibility when examined using fluoroscopic x-ray equipment. This added barium sulphate will not affect the mechanical and electrical properties of the silicone.

As described above, it is desirable to increase the Q factor of a sensor, and the Q factor can be increased by suitable selection of sensor materials or a coating, or both. Preferably both are used, because the resulting high Q factor of a sensor prepared in this fashion is especially suitable for the applications described.

When introduced into the artery, the pressure sensor can provide pressure-related data by use of an external measuring device. As disclosed in the Allen et al. patent, several different excitation systems can be used. The readout device generates electromagnetic energy that can penetrate through the body's tissues to the sensor's implanted location. The sensor's electrical components can absorb a fraction of the electromagnetic energy that is generated by the readout device via inductive coupling. This coupling will induce a current in the sensor's circuit that will oscillate at the same frequency as the applied electromagnetic energy. Due to the nature of the sensor's electro-mechanical system there will exist a frequency of alternating current at which the absorption of energy from the readout device is at a minimum. This frequency is a function of the capacitance of the device. Therefore, if the sensor's capacitance changes so will the frequency at which it minimally absorbs energy from the readout device. Since the sensor's capacitance is mechanically linked to the fluid pressure at the sensor's surface, a measurement of this frequency by the readout device can give a relative measurement of the fluid pressure. If calibration of the device is performed then an absolute measurement of pressure can be made.

Figure 21:
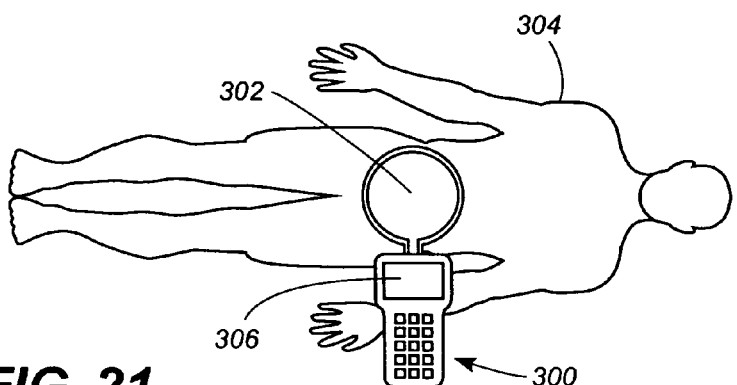
FIG. 21 is a drawing of a read-out device employed according to the invention.

The circuitry used to measure and display pressure is contained within a simple to operate, battery powered, hand-held electronic unit 300, as shown in FIG. 21. This unit 300 also contains the antenna needed to perform the electromagnetic coupling to the sensor. The antenna may be integrated into the housing for the electronics or it may be detachable from the unit so that it can be positioned on the surface of the body 304 in proximity to the implanted sensor 302 and easily moved to optimize the coupling between antenna and sensor. The antenna itself may consist of a simple standard coil configuration or my incorporate ferrous elements to maximize the coupling efficiency. The electronic device would feature an LCD or LED display 306 designed to clearly display the recorded pressure in physiologically relevant units such as mm HG. In an alternative embodiment, the display may be created by integrating a commercially available hand-held computing device such as a Palm® or micro-PC into the electronic circuitry and using this device's display unit as the visual interface between the equipment and its operator. A further advantage of this approach is that the hand-held computer could be detached from the read-out unit and linked to a standard desktop computer. The information from the device could thus be downloaded into any of several commercially available data acquisition software programs for more detailed analysis or for electronic transfer via hard media or the internet to a remote location. In addition, through standard miniaturization techniques, the electronics could be reduced is size such that they are capable of being formed into a band that could be placed around the wrist or leg directly above the location of the implanted sensor. In this manner, continuous readings of pressure could be made and displayed.

Accordingly, the present invention provides for an impedance system and method of determining the resonant frequency and bandwidth of a resonant circuit within a particular sensor. The system includes a transmitting antenna, which is coupled to an impedance analyzer. The impedance analyzer applies a constant voltage signal to the transmitting antenna scanning the frequency across a predetermined spectrum. The current passing through the transmitting antenna experiences a peak at the resonant frequency of the sensor. The resonant frequency and bandwidth are thus determined from this peak in the current.

The method of determining the resonant frequency and bandwidth using an impedance approach may include the steps of transmitting an excitation signal using a transmitting antenna and electromagnetically coupling a sensor having a resonant circuit to the transmitting antenna thereby modifying the impedance of the transmitting antenna. Next, the step of measuring the change in impedance of the transmitting antenna is performed, and finally, the resonant frequency and bandwidth of the sensor circuit are determined.

In addition, the present invention provides for a transmit and receive system and method for determining the resonant frequency and bandwidth of a resonant circuit within a particular sensor. According to this method, an excitation signal of white noise or predetermined multiple frequencies is transmitted from a transmitting antenna, the sensor being electromagnetically coupled to the transmitting antenna. A current is induced in the resonant circuit of the sensor as it absorbs energy from the transmitted excitation signal, the current oscillating at the resonant frequency of the resonant circuit. A receiving antenna, also electromagnetically coupled to the transmitting antenna, receives the excitation signal minus the energy which was absorbed by the sensor. Thus, the power of the received signal experiences a dip or notch at the resonant frequency of the sensor. The resonant frequency and bandwidth are determined from this notch in the power.

The transmit and receive method of determining the resonant frequency and bandwidth of a sensor circuit includes the steps of transmitting a multiple frequency signal from transmitting antenna, and, electromagnetically coupling a resonant circuit on a sensor to the transmitting antenna thereby inducing a current in the sensor circuit. Next, the step of receiving a modified transmitted signal due to the induction of current in the sensor circuit is performed. Finally, the step of determining the resonant frequency and bandwidth from the received signal is executed.

Yet another system and method for determining the resonant frequency and bandwidth of a resonant circuit within a particular sensor includes a chirp interrogation system. This system provides for a transmitting antenna which is electromagnetically coupled to the resonant circuit of the sensor. An excitation signal of white noise or predetermined multiple frequencies is applied to the transmitting antenna for a predetermined period of time, thereby inducing a current in the resonant circuit of the sensor at the resonant frequency. The system then listens for a return signal which radiates from the sensor. The resonant frequency and bandwidth of the resonant circuit are determined from the return signal.

The chirp interrogation method for determining the resonant frequency and bandwidth of a resonant circuit within a particular sensor includes the steps of transmitting a multi-frequency signal pulse from a transmitting antenna, electromagnetically coupling a resonant circuit on a sensor to the transmitting antenna thereby inducing a current in the sensor circuit, listening for and receiving a return signal radiated from the sensor circuit, and determining the resonant frequency and bandwidth from the return signal.

Figure 22:
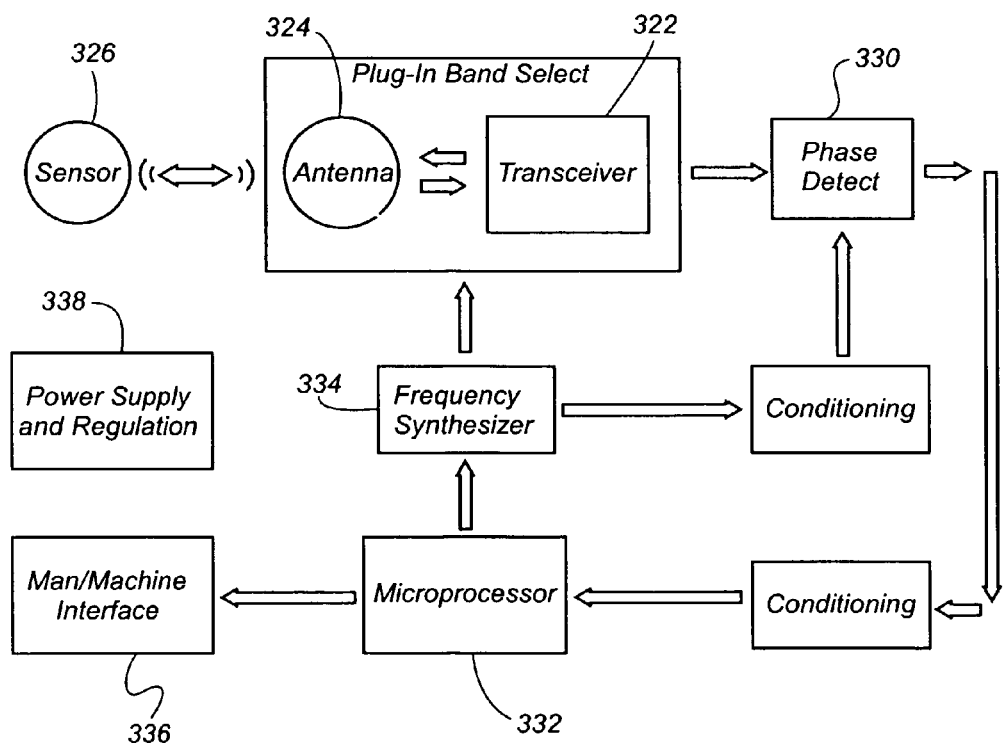
FIG. 22 is a block diagram of an electrical circuit useful according to the invention.

A representative block diagram of an electrical circuit that can be used to interrogate the sensor and determine the resonant frequency is shown in FIG. 22. A transmitter and receiver, i.e., a transceiver 322, has an antenna 324 for generating and receiving signals from a sensor 326. Transceiver 322 is an electronic or digital connection with a phase detector 330, a microprocessor 332, and a frequency synthesizer 334. Microprocessor 332 is in turn connected to an interface 336 such as a terminal. Power supply 338 regulates and provides electrical power to the system.

The present invention also provides an analog system and method for determining the resonant frequency of a resonant circuit within a particular sensor. The analog system comprises a transmitting antenna coupled as part of a tank circuit which in turn is coupled to an oscillator. A signal is generated which oscillates at a frequency determined by the electrical characteristics of the tank circuit. The frequency of this signal is further modified by the electromagnetic coupling of the resonant circuit of a sensor. This signal is applied to a frequency discriminator which in turn provides a signal from which the resonant frequency of the sensor circuit is determined.

The analog method for determining the resonant frequency and bandwidth of a resonant circuit within a particular sensor includes the steps of generating a transmission signal using a tank circuit which includes a transmitting antenna, modifying the frequency of the transmission signal by electromagnetically coupling the resonant circuit of a sensor to the transmitting antenna, and converting the modified transmission signal into a standard signal for further application.

The invention further includes an alternative method of measuring pressure in which a non-linear element such as a diode or polyvinylidenedifloride piezo-electric polymer, is added to the LC circuit. A diode with a low turn-on voltage such as a Schottky diode can be fabricated using micromachining techniques. The presence of this non-linear element in various configurations within the LC circuit can be used to modulate the incoming signal from the receiving device and produce different harmonics of the original signal. The read-out circuitry can be tuned to receive the particular harmonic frequency that is produced and use this signal to reconstruct the fundamental frequency of the sensor. The advantage of this approach is two-fold; the incoming signal can be transmitted continuously and since the return signal will be at different signals, the return signal can also be received continuously.

The above methods lend themselves to the creation of small and simple to manufacture hand-held electronic devices that can be used without complication.

One additional concern regarding devices designated for long term implantation in the human body is maintenance of electrical stability over time as the environment the sensor has been placed in changes. Under this scenario the sensor's accuracy may drift from its original baseline. It would thus be desirable to have available to the user of the device, a method for determining if the sensor is functioning properly and also to be able to recalibrate the device anytime after it has been implanted. This invention therefore also includes a method of using acoustic energy to challenge the sensor and determining to what degree (if any) sensor performance has been degraded. In this method, energy in the ultrasound range is directed towards the sensor and a measurement is made of the mechanical resonance of the sensor membrane. This same measurement can be made at point after the sensor has been implanted. By comparing the values of these two measurements a determination of the degree of change in mechanical resonance frequency can be established. This value can then be used to create a calibration factor that can be applied to the pressure reading taken post-implantation in order to adjust the measured value to reflect the actual pressure within the artery.

The preceding specific embodiments are illustrative of the practice of the invention. It is to be understood, however, that other features and advantages of the present invention may become apparent to those skilled in the art upon examination of the drawings and detailed description above and that all such additional features and advantages, as well as other expedients known to those skilled in the art, may be employed without departing from the spirit of the invention of the scope of the appended claims.

We claim:

1. A sensor for in vivo use within the body of a patient, comprising:
    a first substrate of polyimide, said first substrate having first and second sides;
    a first inductor comprised of a conductive material and disposed on said first side of said first substrate;
    a second substrate of polyimide, said second substrate having first and second sides;
    a second inductor comprised of a conductive material and disposed on said first side of said second substrate;
    said first and second substrates being disposed in parallel, spaced apart relation with said first sides of said substrates in apposition; and
    an intermediate layer disposed between said first and second substrates and maintaining said first and second inductors in spaced-apart relation, said intermediate layer having an opening formed therein such that at least a portion of said first and second inductors are movable toward one another through said opening in response to a change in an external condition.

2. The sensor of claim 1, wherein said intermediate layer comprises an adhesive.

3. The sensor of claim 1, wherein said sensor is enveloped in silicone.

4. The sensor of claim 3, wherein said silicone is approximately 200 microns in thickness.

5. A sensor for in vivo use within the body of a patient, comprising:
    a first substrate of liquid crystal polymer, said first substrate having first and second sides;
    a first inductor comprised of a conductive material and disposed on said first side of said first substrate;
    a second substrate of liquid crystal polymer, said second substrate having first and second sides;
    a second inductor comprised of a conductive material and disposed on said first side of said second substrate;
    said first and second substrates being disposed in parallel, spaced apart relation with said first sides of said substrates in apposition; and
    an intermediate layer disposed between said first and second substrates and maintaining said first and second inductors in spaced-apart relation, said intermediate layer having an opening formed therein such that at least a portion of said first and second inductors are movable toward one another through said opening in response to a change in an external condition.

6. The sensor of claim 5, wherein said intermediate layer comprises a liquid crystal polymer.

7. The sensor of claim 5, wherein said sensor is enveloped in silicone.

8. The sensor of claim 7, wherein said silicone is approximately 200 microns in thickness.

* * * * *